(12) United States Patent
Swartz et al.

(10) Patent No.: US 10,948,494 B2
(45) Date of Patent: Mar. 16, 2021

(54) METHODS FOR ENUMERATION OF RARE CELLS

(71) Applicant: The Board of Trustees of the Leland Stanford Junior University, Stanford, CA (US)

(72) Inventors: James Robert Swartz, Menlo Park, CA (US); Christopher C. Vanlang, Liverpool, NY (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 902 days.

(21) Appl. No.: 15/033,995

(22) PCT Filed: Nov. 7, 2014

(86) PCT No.: PCT/US2014/064658
§ 371 (c)(1),
(2) Date: May 3, 2016

(87) PCT Pub. No.: WO2015/070079
PCT Pub. Date: May 14, 2015

(65) Prior Publication Data
US 2016/0291030 A1    Oct. 6, 2016

Related U.S. Application Data

(60) Provisional application No. 61/901,239, filed on Nov. 7, 2013.

(51) Int. Cl.
*G01N 33/58* (2006.01)
*C12N 7/00* (2006.01)
*G01N 33/574* (2006.01)
*G01N 33/569* (2006.01)

(52) U.S. Cl.
CPC .............. *G01N 33/587* (2013.01); *C12N 7/00* (2013.01); *G01N 33/569* (2013.01); *G01N 33/56966* (2013.01); *G01N 33/574* (2013.01); *G01N 33/581* (2013.01); *C12N 2730/10123* (2013.01); *C12N 2730/10131* (2013.01); *G01N 2333/90241* (2013.01)

(58) Field of Classification Search
None
See application file for complete search history.

(56) References Cited

U.S. PATENT DOCUMENTS

| | | | |
|---|---|---|---|
| 2003/0119077 A1 | 6/2003 | Ts'o et al. | |
| 2007/0087331 A1* | 4/2007 | Bachmann | G01N 33/5052 435/5 |
| 2010/0151472 A1 | 6/2010 | Nolan et al. | |
| 2010/0168402 A1 | 7/2010 | Bundy et al. | |
| 2013/0122492 A1* | 5/2013 | Khosravi | C12Q 1/6806 435/6.11 |

* cited by examiner

*Primary Examiner* — Agnieszka Boesen
(74) *Attorney, Agent, or Firm* — Pamela J. Sherwood; Bozicevic, Field & Francis LLP (57) ABSTRACT

Methods and compositions are provided for the analysis of rare cells or other biological entities in a population, by contacting the population with a labeling nanoparticle comprising a VLP conjugated to a light emitting moiety and a specific binding moiety, then detecting the presence of bound nanoparticle by light emission.

10 Claims, 2 Drawing Sheets
(2 of 2 Drawing Sheet(s) Filed in Color)
Specification includes a Sequence Listing.

SEQUENCE LISTING

```
<160> NUMBER OF SEQ ID NOS: 7

<210> SEQ ID NO 1
<211> LENGTH: 149
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: the non-natural amino acid at this position is
      azidohomoalanine
<220> FEATURE:
<221> NAME/KEY: MISC_FEATURE
<222> LOCATION: (76)..(76)
<223> OTHER INFORMATION: the non-natural amino acid at this position is
      azidohomoalanine

<400> SEQUENCE: 1

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Xaa Gln Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
```

<210> SEQ ID NO 2
<211> LENGTH: 453
<212> TYPE: DNA
<213> ORGANISM: Artificial Sequence
<220> FEATURE:
<223> OTHER INFORMATION: synthetic polynucleotide

<400> SEQUENCE: 2

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac     120
gcgctggaat ctccggaaca ttgttctccg catcacactg cgctgcgtca ggcggtgagc     180
tgctggcgcg aagtgaccga ttttggcgat tgggtgggca acaacatgca ggatcaggcg     240
gcgcgcgatc tggtggtgaa ctatgtgaac gcgaacattg gcctgaaaat tcgtcagctg     300
ctgtggttcc acatctcttg cctgaccttc ggtcgtgaaa ccgttctgga atacctggtt     360
tcttttggtg tttggatttg tactccgccg gcttaccgtc cgccgaacgc accgatcctg     420
agcacccctg cggaaaccac tgttgtgtaa taa                                  453
```

<210> SEQ ID NO 3
<211> LENGTH: 362
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (9)..(9)
<223> OTHER INFORMATION: the non-natural amino acid at this position is
    propargyloxyphenylalanine

<400> SEQUENCE: 3

```
Met Glu Lys Lys Ile Arg Ser Arg Xaa Gly Gly Gly Gly Ser Glu Leu
1               5                   10                  15

Lys His Ser Ile Ser Asp Tyr Thr Glu Ala Glu Phe Leu Gln Leu Val
            20                  25                  30

Thr Thr Ile Cys Asn Ala Asp Thr Ser Ser Glu Glu Leu Val Lys
        35                  40                  45

Leu Val Thr His Phe Glu Glu Met Thr Glu His Pro Ser Gly Ser Asp
    50                  55                  60

Leu Ile Tyr Tyr Pro Lys Glu Gly Asp Asp Ser Pro Ser Gly Ile
65                  70                  75                  80

Val Asn Thr Val Lys Gln Trp Arg Ala Ala Asn Gly Lys Ser Gly Phe
                85                  90                  95

Lys Gln Gly Gly Gly Gly Gly Ser Asp Ile Gln Met Thr Gln Ser Pro
            100                 105                 110

Ser Ser Leu Ser Ala Ser Leu Gly Gly Lys Val Thr Ile Thr Cys Ala
        115                 120                 125

Ser Gln Asp Ile Asn Lys Tyr Ile Ala Trp Tyr Gln His Lys Pro Gly
    130                 135                 140

Lys Gly Pro Arg Leu Leu Ile His Tyr Thr Ser Thr Leu Gln Pro Gly
145                 150                 155                 160

Ile Pro Ser Arg Phe Ser Gly Ser Gly Ser Gly Arg Asp Tyr Ser Phe
                165                 170                 175

Ser Ile Ser Asn Leu Glu Pro Glu Asp Ile Ala Thr Tyr Tyr Cys Leu
            180                 185                 190
```

```
Gln Tyr Asp Asn Leu Tyr Thr Phe Gly Gly Gly Thr Lys Leu Glu Ile
            195                 200                 205
Lys Gly Gly Gly Gly Ser Gly Gly Gly Gly Ser Gly Gly Gly Gly Ser
    210                 215                 220
Glu Val Lys Leu Val Glu Ser Gly Gly Gly Leu Val Gln Pro Gly Gly
225                 230                 235                 240
Ser Leu Ser Leu Ser Cys Ala Ala Ser Gly Phe Thr Phe Thr Tyr Tyr
                245                 250                 255
Met Ser Trp Val Arg Gln Pro Pro Gly Lys Ala Leu Glu Trp Leu Ala
            260                 265                 270
Leu Ile Arg Asn Lys Ala Asn Gly Tyr Thr Thr Glu Tyr Ser Ala Ser
        275                 280                 285
Val Lys Gly Arg Phe Thr Ile Ser Arg Asp Asn Ser Gln Ser Ile Leu
    290                 295                 300
Tyr Leu Gln Met Asn Ala Leu Arg Ala Glu Asp Ser Ala Thr Tyr Tyr
305                 310                 315                 320
Cys Ala Arg Asp Pro Asn Tyr Tyr Asp Gly Ser Tyr Glu Gly Tyr Phe
                325                 330                 335
Asp Tyr Trp Gly Gln Gly Thr Thr Leu Thr Val Ser Ser Gly Gly Gly
            340                 345                 350
Gly Ser Trp Ser His Pro Gln Phe Glu Lys
        355                 360

<210> SEQ ID NO 4
<211> LENGTH: 1084
<212> TYPE: DNA
<213> ORGANISM: Artificial Sequence
<220> FEATURE:
<223> OTHER INFORMATION: synthetic polynucleotide

<400> SEQUENCE: 4
atggagaaaa aaatccgcag tcgttaggga ggaggtggct ctgaactgaa acatagcatc      60
tccgactata ccgaagcgga gtttttacag ctggtgacca cgatttgcaa cgccgatacc     120
tcatcggaga gagctggtg aaattagtga cgcattttga agagatgacc gagcatccga     180
gcggttccga tctgatttac tatccgaaag agggcgatga cgatagcccg agtgggattg     240
ttaacaccgt taaagtggc gtgcggccaa tggtaaaagc gggtttaaac aaggggtgg      300
cggtggatcc gatattcaaa tgacccgagc cccgagctcc ctgagcgcga gcctggggg     360
caaagtgacc attacctgca agcgagccag gacatcaata gtatatcgc gtggtatcag     420
cataaacccg gcaaaggccc tcgtctgctg atccattata ccagcaccct tcagccgggc    480
atcccgagcc gttttagcgg cagcggaacg gacgtgatta gcttcagc attagcaatc     540
tggaaccgga agatattgca acgtactatt gcctgcaata tgataatctg tatacctttg   600
ggggtgggac caagcttgag attaaagggg gaggcgctcc ggtggcggtg ggagcggcgg    660
aggtggcagc gaagtgaaac tagttgaatc cggagggggt cttgtccagc caggggctc    720
actgtcgctg tcatgcgcag cgagcggctt taccttcacc gatattacat gagctgggtg   780
cgtcaaccgc ctggcaaggc gctggagtgg ctggcgctga ttcgtaataa agcgaacggc   840
tacacaacgg aatatagtgc gagcgtgaaa ggccgtttca ccatttctct gataatagcc   900
agagcattct gtatcttcag atgaatgcgc tgcgtgcgga agatagcgcg acctattatt   960
gtgcgcgtga tccaactat tatgatggca gttatgaagg ctattttgat tattgggcca   1020
gggtaccacc tgaccgtga gcagcggtgg cggtggcagc tggagccacc cgcagttcga   1080
``` aaag                                                                              1084

<210> SEQ ID NO 5
<211> LENGTH: 182
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: the non-natural amino acid at this position is
      homopropargylglycine
<220> FEATURE:
<221> NAME/KEY: MISC_FEATURE
<222> LOCATION: (170)..(170)
<223> OTHER INFORMATION: the non-natural amino acid at this position is
      homopropargylglycine

<400> SEQUENCE: 5

Xaa Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
            20                  25                  30

Gly Lys Lys Leu Pro Leu Glu Val Leu Lys Glu Leu Glu Ala Asn Ala
        35                  40                  45

Arg Lys Ala Gly Cys Thr Arg Gly Cys Leu Ile Cys Leu Ser His Ile
    50                  55                  60

Lys Cys Thr Pro Lys Leu Lys Lys Phe Ile Pro Gly Arg Cys His Thr
65                  70                  75                  80

Tyr Glu Gly Asp Lys Glu Ser Ala Gln Gly Ile Gly Glu Ala Ile
                85                  90                  95

Val Asp Ile Pro Glu Ile Pro Gly Phe Lys Asp Leu Glu Pro Leu Glu
            100                 105                 110

Gln Phe Ile Ala Gln Val Asp Leu Cys Val Asp Cys Thr Thr Gly Cys
        115                 120                 125

Leu Lys Gly Leu Ala Asn Val Gln Cys Ser Asp Leu Leu Lys Lys Trp
    130                 135                 140

Leu Pro Gln Arg Cys Ala Thr Phe Ala Ser Lys Ile Gln Gly Gln Val
145                 150                 155                 160

Asp Lys Ile Lys Gly Ala Gly Gly Asp Xaa Gly Arg Ser Arg Trp Ser
                165                 170                 175

His Pro Gln Phe Glu Lys
            180

<210> SEQ ID NO 6
<211> LENGTH: 546
<212> TYPE: DNA
<213> ORGANISM: Artificial Sequence
<220> FEATURE:
<223> OTHER INFORMATION: synthetic polynucleotide

<400> SEQUENCE: 6
atgaaaccaa cagaaaataa cgaagacttc aacatcgtgg ccgtggccag caacttcgcg      60
accacggatc tcgatgctga ccgcgggaag ttgcccggca agaagctgcc gctggaggtg     120
ctcaaagagc tggaagccaa tgcccggaaa gctggctgca ccaggggctg tctgatctgc     180
ctgtcccaca tcaagtgcac gcccaagctg aagaagttca tcccaggacg ctgccacacc     240
tacgaaggcg acaagagtc cgcacagggc ggcataggcg aggcgatcgt cgacattcct     300
gagattcctg ggttcaagga cttggagccc ctggagcagt tcatcgcaca ggtcgatctg     360

```
tgtgtggact gcacaactgg ctgcctcaaa gggcttgcca acgtgcagtg ttctgacctg      420
ctcaagaagt ggctgccgca acgctgtgcg acctttgcca gcaagatcca gggccaggtg      480
gacaagatca aggggccgg tggtgacatg ggtcgtagtc gctggagcca cccgcagttc       540
gaaaag                                                                546

<210> SEQ ID NO 7
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 7

Trp Ser His Pro Gln Phe Glu Lys
1               5
```

METHODS FOR ENUMERATION OF RARE CELLS

GOVERNMENT RIGHTS

This invention was made with Government support under contracts HG000044 and CA151459 awarded by the National Institutes of Health. The Government has certain rights in the invention.

BACKGROUND OF THE INVENTION

The term cancer refers to diseases in which abnormal cells divide without control and are able to invade other tissues. Cancer cells originating at one site can metastasize to other sites through the blood and lymph systems. The term refers to a diverse collection of diseases, including carcinomas, sarcomas, leukemias, lymphomas, gliomas, etc. Detection and appropriate treatment rely on the ability to accurately diagnose the severity, metastasis, and nature of the individual disease.

Peripheral blood circulating tumor cells (CTCs) recently have been detected and shown to have prognostic and predictive value in breast and prostate cancer. These rare cells have detached from the primary tumor, and may include the tumor initiating cells that cause metastatic lesions. As the management of metastatic disease is a major medical concern, having the ability to rapidly detect, count, and isolate CTCs from a mixture of cells is of great importance to those in cancer biology.

In spite of the diagnostic potential of CTCs, the existing procedures to detect CTCs are slow, expensive, and imprecise. These methods take several hours to sufficiently capture CTCs by sorting sequentially through the blood. Afterwards, enumeration requires fluorescent-microscopy to visualize and identify cells. These steps cause the response time to take a matter of days and prevent the ability to isolate live cells. These factors result in an underrepresentation of the number and diversity of CTCs as well as impede doctors from providing their patient information in a timely manner.

Conventional methods rely on antibody capture of CTCs using an anti-epithelial cell adhesion molecule ($\alpha$-EpCAM) to bind to epithelial cells, which are absent in blood cells. However, the use of EpCAM overlooks the types of cancer cells that undergo an epithelial-mesenchymal transition. These factors can result in an underrepresentation of the number and diversity of CTCs as well as impede doctors from providing their patient information in a timely manner.

Therefore, there is a need to develop simple yet highly sensitive and specific cancer detection systems and methods to overcome the above and other problems. The detection systems and methods can be used as a diagnostic, prognostic or predictive assay in patients.

SUMMARY OF THE INVENTION

Methods and compositions are provided for the collection, detection, analysis and/or characterization of rare cells or other biological entities in a population. More specifically, the invention is directed to a method for diagnosing the presence of rare cells, including without limit cancer cells, in a biological sample. The method of the invention provides highly sensitive and rapid analytical techniques, optionally in the absence of affinity based enrichment steps. According to one embodiment, the method of the invention enables assaying whole blood for cancer staging, monitoring and screening. The sensitive nature of the assay facilitates the detection of residual disease, thus making it possible to monitor for cancer recurrence.

In some embodiments of the invention, a biological specimen is obtained from an individual, where the biological specimen comprises a cell population suspected of having a rare cell or biological entity of interest. In some embodiments, the biological sample is blood. The biological sample may then be analyzed to determine the presence and number of the rare cell or biological entity by contacting with a labeling nanoparticle of the invention, and quantitating the presence and optionally distribution of light produced by the labeling nanoparticle. Alternatively the population is contacted with the labeling nanoparticle under cross-link conditions, resulting in aggregation of the rare cell or biological entity for separation purposes.

For use in the methods of the invention, a population is contacted with a labeling nanoparticle, which nanoparticle comprises a virus-like particle (VLP) conjugated to at least one, usually a plurality, of a specific binding moiety and at least one, usually a plurality, of a light producing moiety. The specific binding moiety specifically and selectively binds to the rare cell or biological entity of interest, i.e. it binds to the cell or biological entity of interest at a detectably higher level than it binds to the population in which the rare cell or entity is found. The light producing moiety provides a detectable label, which can be captured by CCD or other light gathering imaging systems. Luciferase is an exemplary light producing moiety. In some cases, also, two or more different binding moieties may be used to enhance VLP adhesion selectivity to specific target cells.

In some embodiments, the population of cells or biological entities are collected on a membrane surface prior to contacting with the labeling nanoparticles, allowing resolution of individual cells or biological entities by detection of light emission.

In other embodiments, the population of cells or biological entities are contacted in suspension. In such an embodiment, the cells or biological entities can aggregate. Aggregations can be recovered by standard differential centrifugation techniques; or can be collected on a membrane for detection of light emission, e.g. by measuring the total light produced by the sample.

In some embodiments of the invention, the rare cell is a circulating cancer cell. The method of the invention may be used to assess residual cancer cells in circulation following medical, radiation, or surgical treatment to eradicate the tumor. The method may be also be performed periodically over a course of years to assess the patient for the presence and number of tumor cells in the circulation as an indicator of occurrence, recurrence and/or progression of disease. The method is also useful for diagnosing cancer or predicting a disease outcome from a patient blood sample.

In other embodiments the rare cell is a stem cell, e.g. a circulating hematopoietic stem cell. In other embodiments the rare biological entity is a virus or bacteria, e.g. a pathogen for which screening is desired.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Rapid and specific detection and enumeration of rare cells is of interest for various purposes, including clinical uses. For example the presence of tumor cells in the circulation can be used to screen for cancer in place of, or in conjunction with, other tests, such as mammography, measurements of PSA, etc. By employing appropriate binding partners directed to specific markers on cells, the organ origin of such cells may readily be determined, e.g., breast, prostate, colon, lung, ovarian or other non-hematopoietic cancers. Thus, in cases where cancer cells can be detected, while there are essentially no clinical signs of a tumor, it will be possible to identify their presence as well as the organ of origin. Screening can be done with the relatively simple blood test of the present invention described herein, which functions with a high degree of sensitivity.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control. Measuring emission of light, either integrated total emission or detection of particles corresponding to rare cells or biological entities may be performed.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

As used herein, the term "rare cell" or biological entity refers to a cell or biological entity that can be distinguished on the basis of a cell surface marker from the population of cells in which it is found, and which is present in the population at a low number. Usually a rare cell constitutes not more than 1 in $10^5$ cells in the population. The methods of the invention allow detection of a rare cell that is from about 1 in $10^5$ cells in the population, to about $1/10^{19}$ cells in the population; detection of a rare cell that is from about 1 in $10^5$ cells in the population, to about $1/10^9$ cells in the population; detection of a rare cell that is from about 1 in $10^5$ cells in the population, to about $1/10^8$ cells in the population.

Rare cells of interest include stem cells, circulating tumor cells, specific immune cells (for example B cells or T cells that specifically bind to an antigen of interest, including without limitation autoantigen specific T cells or B cells), and the like. Rare biological entities of interest include bacteria, protozoan pathogens, viruses, and the like.

To "analyze" includes determining a set of values associated with a sample by measurement of light emitted by bound labeling nanoparticles in the sample, and comparing the measurement against measurement in a sample or set of samples from the same subject, from a control, from reference values, etc. as known in the art. To "analyze" can include performing a statistical analysis.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A labeling nanoparticle of the invention comprises a virus-like particle (VLP) conjugated to at least one, usually a plurality, of a specific binding moiety and at least one, usually a plurality, of a light producing moiety. The specific binding moiety specifically and selectively binds to the rare cell or biological entity of interest. The light producing moiety provides a detectable label, which can be captured by CCD or other light gathering imaging systems.

As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. The capsid may be empty, or contain non-viral components, e.g. mRNA fragments, etc. A preferred virus protein for assembly into a VLP is Hepatitis B core protein, although other virus proteins also find use for this purpose.

The specific binding moiety and the light producing moiety are conjugated to a VLP. Preferably the binding moiety and the light producing moiety, e.g. luciferase, are directly conjugated to the VLP through covalent bonds. Conveniently, an unnatural amino acid and CLICK chemistry is used to make a stable labeling nanoparticle for these purposes. An advantage of the methods of the invention is the ability to generate a nanoparticle with multiple labeling and affinity moieties on a single nanoparticle, e.g. at least about 5 conjugated moieties, at least about 10 conjugated moieties, at least about 20 conjugated moieties, at least about 30 conjugated moieties, at least about 40 conjugated moieties, at least about 60 conjugated moieties, at least about 60 conjugated moieties, where the distribution between light producing moiety and specific binding moiety may be 1:1, 2:1, 1:2, 3:1, 1:3, 5:1, 1:5, etc. as desired for the specific purpose.

A stable labeling nanoparticle maintains the association of proteins in a capsid structure under physiological conditions for extended periods of time, e.g. for at least about 24 hrs, at least about 1 week, at least about 1 month, or more. Once assembled, the nanoparticles can have a stability commensurate with the native virus particle and, in some cases, exceed that stability, e.g. upon exposure to pH changes, heat, freezing, ionic changes, etc.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

As used herein, the terms "purified" and "isolated" when used in the context of a polypeptide that is substantially free of contaminating materials from the material from which it was obtained, e.g. cellular materials, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide that is chemically synthesized refers to a polypeptide which is substantially free of chemical precursors or other chemicals which are involved in the syntheses of the polypeptide.

The polypeptides to generate the labeling nanoparticle may be isolated and purified in accordance with conventional methods of recombinant synthesis or cell free protein synthesis. Exemplary coding sequences are provided, however one of skill in the art can readily design a suitable coding sequence based on the provided amino acid sequences. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

Viral proteins for use in the methods of the invention may comprise one or more unnatural amino acids at a predetermined site, and may comprise or contain 1, 2, 3, 4, 5 or more unnatural amino acids. If present at two or more sites in the polypeptide, the unnatural amino acids can be the same or different.

Unnatural amino acids of interest include, without limitation, amino acids that provide a reactant group for CLICK chemistry reactions (see *Click Chemistry: Diverse Chemical Function from a Few Good Reactions* Hartmuth C. Kolb, M. G. Finn, K. Barry Sharpless Angewandte Chemie International Edition Volume 40, 2001, P. 2004, herein specifically incorporated by reference). For example, the amino acids azidohomoalanine, p-acetyl-L-phenylalanine and p-azido-L-phenylalanine are of interest. In some embodiments, the unnatural amino acid is introduced by global replacement of methionine on the protein, e.g. methionine can be left out of a cell-free reaction mixture, and substituted by from 0.25-

2.5 mM azidohomoalanine (AHA). Alternatively the unnatural amino acid is introduced by orthogonal components, as known in the art.

The binding moiety and the detectable label may comprise a complementary active group for CLICK chemistry conjugation to the viral polypeptide of the invention. For example, it may be synthesized with one or more unnatural amino acids, which allow for the conjugation to the unnatural amino acid present on the viral protein. One of skill in the art will understand that the chemistry for conjugation is well-known and can be readily applied to a variety of groups, e.g. detectable label, antibody, polypeptide, etc.

The term "binding partner" or "specific binding moiety," as used herein, refers to a molecule or moiety that specifically recognizes and binds to the rare cell or biological entity of interest, and exhibits negligible cross-reactivity with other molecules or substances that may be present in the sample being tested. Typical binding partners include, but are not limited to, antigens, antigen fragments, receptors, nucleic acids, and polyclonal antibodies, monoclonal antibodies, antibody fragments, lectins, protein A, protein G, polypeptides, avidin, streptavidin, cyclodextrans, and crown ethers, intrinsic factor, folate and binding protein. A binding partner specific for a given analyte may be obtained from commercial sources or may be prepared in accordance with standard procedures known to those skilled in the art. Examples of analyte:binding partner pairs include, but are not limited to, hapten:antibody, biotin:avidin, hormone:receptor, polypeptide:antibody, and oligonucleotide:complementary DNA or RNA.

The term "antibody," as used herein, refers to immunoglobulins that are produced in response to the detection of a foreign substance, and includes intact molecules as well as functional fragments thereof, such as Fab, F(ab')$_2$, and Fv, single chain Fv, etc.

Tumor markers to which antibodies may be directed include proteins present selectively on cancer cells, including, but not limiting to, alpha-fetoprotein (AFP), beta-HCG, bladder tumor antigen (BTA), CA 15-3, CA 27.29, CA 125, CA 72-4, CA 19-9, calcitonin, carcinoembryonic antigen (CEA), chromogranin A, epidermal growth factor receptor (EGFR), hormone receptors, HER2 (also known as HER2/neu, erbB-2, or EGFR2), human chorionic gonadotropin (HCG), immunoglobulins, neuron-specific enolase (NSE), NMP22, prostate-specific antigen (PSA), prostatic acid phosphatase (PAP), prostate-specific membrane antigen (PSMA), S-100, TA-90, thyroglobulin, and the like.

An "effective amount" or a "sufficient amount" of a substance is that amount sufficient to cause a desired biological effect, such as beneficial results, including clinical results, and, as such, an "effective amount" depends upon the context in which it is being applied. In the context of this invention.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc. Also included are mammals such as domestic and other species of canines, felines, and the like.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Using breast cancer as an example, such antibodies may include anti-MUC-1, anti-estrogen receptor, anti-progesterone receptor, anti-CA27.29, anti-CA15.5, anti-cathepsin D, anti-p53, anti-urokinase type plasminogen activator, anti-epidermal growth factor, anti-epidermal growth factor receptor, anti-BRCA1, anti-BRCA2, anti-prostate specific antigen, anti-plasminogen activator inhibitor and/or anti-Her2-neu antibodies. Additional markers for aggressiveness and invasiveness are Lewis a (Lea), sialyl Lewis a (sLea), the intergrins (CD49b, CD49c, CD29), gelatinase A and B (MMP-2, MMP-9), tissue collagenase (MMP-1), fibroblast activation protein (FAP), guanidinobenzoatase, CEA, S100 family (S100A4, mtsl, 18A2/mtsl, pEL-98, p9Ka, metastasin), the Cyclins A and E, p27, p53, vascular endothelilal growth factor (VGEF) and E-Cadherin.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Methods of Analysis

In the methods of the invention, a biological sample suspected of comprising a rare cell or biological entity is contacted with a labeling nanoparticle of the invention. The biological sample is obtained from any convenient source. In some embodiments, the sample is blood, e.g. mammalian blood, including human blood. The blood sample may be treated in accordance with conventional practices, e.g. lysis of red blood cells, etc. Conveniently the sample is a standard blood draw, e.g. about 5 to about 10 ml. of whole blood, although smaller and larger samples also find use.

A sample will usually comprise at least about $10^4$ cells, at least about $10^5$ cells, at least about $5 \times 10^5$ cells, and not more than about $10^{10}$ cells, not more than about $10^9$ cells, not more than about $10^8$ cells. The cells may be suspended in a suitable medium that maintains structural integrity, e.g. media, PBS, normal saline, and the like as known in the art. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeling nanoparticles are added to a suspension of cells, and incubated for a period of time sufficient to bind the available cell surface antigens. The incubation will usually be at least about 5 minutes and usually less than about 30 minutes. It is desirable to have a sufficient concentration of nanoparticles in the reaction mixture, such that the efficiency of the separation is not limited by lack of nanoparticles. The appropriate concentration is determined by titration.

The population is usually washed of unbound nanoparticles, e.g. by pelleting and resuspension in fresh medium, etc., and may be washed one or more times as required to reduced background to a desirable level.

In some embodiments the population is captured on a membrane prior to contacting with the labeling nanoparticle. In other embodiments the population is captured on a membrane following contacting with the labeling nanoparticle. In yet other embodiments, the suspension is allowed to aggregate and the aggregated cells are collected by differential centrifugation, etc., as known in the art.

The dimensions and pore size of the capture membrane will vary with the nature of the cell or biological entity to be analyzed. Where rare mammalian cells are analyzed, the pore size may be up to about 1.2 micron or smaller. Where bacterial cells or viruses are analyzed, a smaller pore size is desirable, e.g. up to about 0.2 micron pores. Such filters are readily available and known to those of skill in the art.

The overall dimensions can vary with the size of the sample. For example, a 96 well plate, 7.5 mm diameter filter is convenient for multiplex analysis. However the methods also find use with smaller sizes, e.g. from about 1 mm to about 5 mm diameter, up to much larger sizes, e.g. from about 10 mm to 100 mm diameter or may be in a rectangular format of various dimensions to allow optimal use of the imaging device.

The light emitting moiety may require contacting with a substrate in order to emit light.

Luciferase is a moiety of particular interest. Firefly luciferase is isolated from beetles (*Photinus pyralis*), while *Renilla* luciferase is from sea pansy (*Renilla reniformis*). These enzymes differ in their substrate and cofactor requirements. Firefly luciferase uses luciferin in the presence of oxygen, ATP and magnesium to produce light, while *Renilla* or *Gaussia* luciferase requires only coelenterazine and oxygen. Firefly luciferase produces a greenish yellow light in the 550-570 nm range. *Renilla* luciferase produces a blue light of 480 nm. These enzymes can be used in dual-reporter assays due to their differences in substrate requirements and light output. The sample is contacted with an effective amount of the substrate, and if required with ATP and magnesium, in order to produce light.

The emitted light is detected by any convenient method, particularly a CCD camera that can integrate the total light from a sample, or detect distinct spots of light. The collected data may be compared to a control or reference for calibration.

The presence of light is indicative of the presence of the rare cell or biological entity, and can be used to calculate the number and binding properties of the rare cell or biological entity. For example, a differential image analysis may be performed as to the presence of pathogenic markers on bacterial cells or virus in a blood sample, circulating cancer cells may be detected and classified as the presence of a marker of interest, and the like.

Also within the scope of the invention are kits comprising the compositions (e.g., labeling nanoparticles and formulations thereof) of the invention and instructions for use. The kit can further contain a least one additional reagent, e.g. luciferin, coelenterazine, etc. Kits typically include a label indicating the intended use of the contents of the kit. The term label includes any writing, or recorded material supplied on or with the kit, or which otherwise accompanies the kit.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Luminescent nanoparticles were prepared using VLP nanoparticle technology. These nanoparticles were functionalized by direct conjugation of *Gaussia* luciferase (see Goerke et al. 2008, Metabolic Engineering, 10(3-4): 187-200) and binding domains, the IM9-scFv 38c13 fusion protein (see Patel et al., 2009, BBRC 390 971-6) to stabilized HepBc VLPs. These nanoparticles have high selectivity for white blood cells with a specific surface marker, the S1C5 antibody (recognized by the 38C13 scFv). These nanoparticles are selectively and specifically recognized and adhere to the marked cells. Using a CCD camera, distinct spots of light were observed. The number of spots correlates with the expected number of marked cells. These rapid enumeration and flocculation methods are useful for point of care diagnostic and collection tools to assist the active surveillance of cancers and to examine the effectiveness of treatments.

Materials and Methods

Plasmid construction. The sequence encoding the human Hepatitis B core (HBc) capsid monomer of subtype adyw (Pasek et al., 1979 Nature 282(5739): 575-9) with the C-terminus truncated at amino acid 149 was optimized for *E. coli* tRNA concentrations and synthesized from oligonucleotides designed with DNAworks v3.0. The vector pET24a-HBc149 was generated by ligation (T4 DNA ligase, New England Biolabs, Ipswich, Mass.) of the optimized HBc protein gene into the pET-24a(+) vector (Novagen, San Diego, Calif.) at the Nde I and Xho I restriction sites. To incorporate methionine analogues, two mutations (M66S and L76M) were introduced (see, for example, provisional patent application 61/755,850, herein specifically incorporated by reference).

DNA sequences for the 38C13 tumor idiotype scFv (in the Vl-Vh gene order) were codon-optimized for expression in *E. coli* using DNAworks. Overlapping oligonucleotides were designed for PCR-based gene synthesis using DNAworks. The DNA sequence encoding the 38C13 scFv was PCR amplified from oligonucleotides using a two step PCR-based gene synthesis method (Patel et al. (2009) supra). The PCR product was digested with restriction endonucleases NdeI and XhoI and cloned into a pY71 expression vector digested with NdeI and SalI (Kuchenreuther et al. 2009, PLoS ONE 4(10) e7565). The DNA sequence encoding the luficerase from *G. princeps* was a gift from Dr. Bruce Bryan (NanoLight Technologies). The gene codes for the expected mature form of the protein and has the predicted N-terminal signal peptide domain replaced with a single start codon. The DNA sequence was PCR amplified, digested, and ligated into a pET24a expression vector. Plasmids were transformed into DH5α cells (One Shot MAXX Efficiency DH5 α-T1R Competent Cells, Invitrogen, Carlsbad, Calif.) and purified with Plasmid Maxi Kits (Qiagen, Valencia, Calif.). All mutants were constructed using QuikChange PCR (Stratagene, La Jolla, Calif.).

Sequences of proteins. Shown are the sequences of HBc protein, 38C13 tumor idiotype scFv, and *Gaussia* luciferase with the non-natural amino acid incorporation sites. The non-natural amino acid used in the HBc is azidohomoalanine (AHA), a methionine analogue. The non-natural amino acid used in the 38C13 scFv is propargyloxyphenylalanine and is symbolized as "Z" in the protein primary sequence. The non-natural amino acid used in the *Gaussia* Luciferase is homopropargylglycine (HPG), a methionine analogue. Linkers are underlined. The Strep II purification tag has the sequence WSHPQFEK.

| Name | Protein Sequence | DNA encoding sequence |
|---|---|---|
| SS1(HP) 78AHA (HBc149) | (SEQ ID NO: 1) (AHA)DIDPYKEFGATV ELLSFLPSDFFPSVRCL LDTAAALYRDALESPEH CSPHHTALRQAVSCWRE VTDFGDWVGNN(AHA)Q DQAARDLVVNYVNANIG LKIRQLLWFHISCLTFG RETVLEYLVSFGVWICT PPAYRPPNAPILSTLPE TTVV | (SEQ ID NO: 2) ATGGATATCGACCCGTACAAAGAATTCGGCGCGACCGTTGAACTGC TGTCTTTCCTGCCGTCTGATTTCTTCCCGTCTGTTCGTTGCCTGCT GGACACCGCGGCAGCACTGTACCGTGACGCGCTGGAATCTCCGGAA CATTGTTCTCCGCATCACACTGCGCTGCGTCAGGCGGTGAGCTGCT GGCGCGAAGTGACCGATTTTGGCGATTGGGTGGGCAACAACATGCA GGATCAGGCGGCGCGCGATCTGGTGGTGAACTATGTGAACGCGAAC ATTGGCCTGAAAATTCGTCAGCTGCTGTGGTTCCACATCTCTTGCC TGACCTTCGGTCGTGAAACCGTTCTGGAATACCTGGTTTCTTTTGG TGTTTGGATTTGTACTCCGCCGGCTTACCGTCCGCCGAACGCACCG ATCCTGAGCACCCTGCCGGAAACCACTGTTGTGTAATAA |

-continued

| Name | Protein Sequence | DNA encoding sequence |
|---|---|---|
| 38C13-<br>IM9-<br>scFv-N1 | (SEQ ID NO: 3)<br>MEKKIRSRZGGGGSELK<br>HSISDYTEAEFLQLVTT<br>ICNADTSSEEELVKLVT<br>HFEEMTEHPSGSDLIYY<br>PKEGDDDSPSGIVNTVK<br>QWRAANGKSGFKQGGGG<br>UDIQMTQSPSSLSASL<br>GGKVTITCASQDINKYI<br>AWYQHKPGKGPRLLIHY<br>TSTLQPGIPSRFSGSGS<br>GRDYSFSISNLEPEDIA<br>TYYCLQYDNLYTFGGGT<br>KLEIKGGGGSGGGGSGG<br>GGSEVKLVESGGGLVQP<br>GGSLSLSCAASGFTFTY<br>YMSWVRQPPGKALEWLA<br>LIRNKANGYTTEYSASV<br>KGRFTISRDNSQSILYL<br>QMNALRAEDSATYYCAR<br>DPNYYDGSYEGYFDYWG<br>QGTTLTVSSGGGGSWSH<br>PQFEK | (SEQ ID NO: 4)<br>ATGGAGAAAAAAATCCGCAGTCGTTAGGGAGGAGGTGGCTCTGAAC<br>TGAAACATAGCATCTCCGACTATACCGAAGCGGAGTTTTTACAGCT<br>GGTGACCACGATTTGCAACGCCGATACCTcaTCGGAGAAGAGCTGG<br>TGAAATTAGTGACGCATTTTGAAGAGATGACCGAGCATCCGAGCGG<br>TTCCGATCTGATTTACTATCCGAAAGAGGGCGATGACGATAGCCCG<br>AGTGGGATTGTTAACACCGTTAAAAGTGGCGTGCGGCCAATGGTAA<br>AAGCGGGTTTAAACAAGGGGGTGGCGGTGGATCCGATATTCAAATG<br>ACCCAGAGCCCGAGCTCCCTGAGCGCGAGCCTGGGGGGCAAAGTGA<br>CCATTACCTGCAAGCGAGCCAGGACATCAATAAGTATATCGCGTGG<br>TATCAGCATAAACCCGGCAAAGGCCCTCGTCTGCTGATCCATTATA<br>CCAGCACCCTTCAGCCGGGCATCCCGAGCCGTTTTAGCGGCAGCGG<br>AACGGACGTGATTATAGCTTCAGCATTAGCAATCTGGAACCGGAAG<br>ATATTGCAACGTACTATTGCCTGCAATATGATAATCTGTATACCTT<br>TGGGGGTGGGACCAAGCTTGAGATTAAAGGGGGAGGCGCTCCGGTG<br>GCGGTGGGAGCGGCGGAGGTGGCAGCGAAGTGAAACTAGTTGAATC<br>CGGAGGGGGTCTTGTCCAGCCAGGGGGCTCACTGTCGCTGTCATGC<br>GCAGCGAGCGGCTTTACCTTCACCGATATTACATGAGCTGGGTGCG<br>TCAACCGCCTGGCAAGGCGCTGGAGTGGCTGGCGCTGATTCGTAAT<br>AAAGCGAACGGCTACACAACGGAATATAGTGCGAGCGTGAAAGGCC<br>GTTTCACCATTTCTCTGATAATAGCCAGAGCATTCTGTATCTTCAG<br>ATGAATGCGCTGCGTGCGGAAGATAGCGCGACCTATTATTGTGCGC<br>GTGATCCCAACTATTATGATGGCAGTTATGAAGGCTATTTTGATTA<br>TTGGGCCAGGGTACCACCCTGACCGTGAGCAGCGGTGGCGGTGGCA<br>GCTGGAGCCACCCGCAGTTCGAAAAG |
| Gaussia<br>Luciferase<br>S4 | (SEQ ID NO: 5)<br>(HPG)KPTENNEDFNIV<br>AVASNFATTDLDADRGK<br>LPGKKLPLEVLKELEAN<br>ARKAGCTRGCLICLSHI<br>KCTPKLKKFIPGRCHTY<br>EGDKESAQGGIGEAIVD<br>IPEIPGFKDLEPLEQFI<br>AQVDLCVDCTTGCLKGL<br>ANVQCSDLLKKWLPQRC<br>ATFASKIQGQVDKIKGA<br>GGD(HPG)GRSRWSHPQ<br>FEK | (SEQ ID NO: 6)<br>ATGAAACCAACAGAAAATAACGAAGACTTCAACATCGTGGCCGTGG<br>CCAGCAACTTCGCGACCACGGATCTCGATGCTGACCGCGGGAAGTT<br>GCCCGGCAAGAAGCTGCCGCTGGAGGTGCTCAAAGAGCTGGAAGCC<br>AATGCCCGGAAAGCTGGCTGCACCAGGGGCTGTCTGATCTGCCTGT<br>CCCACATCAAGTGCACGCCCAAGCTGAAGAAGTTCATCCCAGGACG<br>CTGCCACACCTACGAAGGCGACAAAGAGTCCGCACAGGGCGGCATA<br>GGCGAGGCGATCGTCGACATTCCTGAGATTCCTGGGTTCAAGGACT<br>TGGAGCCCCTGGAGCAGTTCATCGCACAGGTCGATCTGTGTGTGGA<br>CTGCACAACTGGCTGCCTCAAAGGGCTTGCCAACGTGCAGTGTTCT<br>GACCTGCTCAAGAAGTGGCTGCCGCAACGCTGTGCGACCTTTGCCA<br>GCAAGATCCAGGGCCAGGTGGACAAGATCAAGGGGGCCGGTGGTGA<br>CATGGGTCGTAGTCGCTGGAGCCACCCGCAGTTCGAAAAG |

Cell-free protein synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 45 µg/mL plasmid, approximately 100-300 µg/mL T7 RNA polymerase, 2 mM of each of the 20 unlabeled amino acids, 0.33 mM NAD, 0.26 mM Coenzyme A (CoA), 2.7 mM potassium oxalate, and 0.24 volumes of E. coli KC6 S30 extract (Goerke and Swartz 2008) and with or without 21 µM L-[U-$^{14}$C]-leucine (Amersham Pharmacia, Uppsala, Sweden).

To encourage formation of disulfide bonds for production of the IM9-scFv and the luciferase, the cell extract was first pretreated at room temperature for 30 min with 50 µM iodoacetamide. A glutathione buffer (4 mM oxidized glutathione (GSSG) and 1 mM reduced glutathione (GSH)) was then added to the reaction to stabilize the thiol/disulfide redox potential and finally DsbC, a periplasmic disulfide bond isomerase was added to a final concentration of 100 µg/mL. For global replacement of methionines in HBc proteins, methionine was left out of cell-free reaction mixtures, and substituted by 1 mM azidohomoalanine (AHA) (Medchem Source LLP, Federal Way, Wash.), a non-natural amino acid that displays an azide moiety.

For global replacement of methionines in GLuc protiens, methionine was left out of the cell-free reaction mixtures, and substituted by 1 mM homopropargylglycine (HPG). For p-propargyloxyphenylalanine (PPF) incorporation 4 mM PPF and 500 µg/mL tRNA synthetase were added to cell-free reactions. Purified tRNA synthetase (PpaRS-His), formulated in 10 mM potassium phosphate buffer, pH 8 with 20% sucrose was added. All reagents were obtained from Sigma-Aldrich (St. Louis, Mo.) unless otherwise noted.

CFPS reactions to produce the HBc protein were conducted without modifications to encourage disulfide bond formation at 30° C. for 6 h. Small-scale CFPS reactions were carried out in 20 µL volumes in 1.5 mL microcentrifuge tubes. Preparative-scale reactions used 6 mL volumes with 1 mL per well in 6-well tissue culture plates (BD Falcon #3046, BD, Franklin Lakes, N.J.). 8.4 µM L-[U-$^{14}$C]-Leucine (PerkinElmer, Waltham, Mass.) was added to small-scale reactions and to 20 µL aliquots of preparative-scale reactions for measuring protein yields using a previously described trichloroacetic acid protein precipitation protocol (Calhoun and Swartz 2005) and a Beckman LS3801 liquid scintillation counter (Beckman Coulter, Fullerton, Calif.). To remove unincorporated L-[U-$^{14}$C] leucine, the cell-free product was immediately dialyzed in 6-8000 MWCO Spectra/Pro Molecularporous Membrane Tubing (Spectrum Labs, Rancho Dominguez, Calif.) against Dialysis Buffer (10 mM Tris-HCl, pH 7.4, 1.5 M NaCl) with 1 mM DTT with 2 buffer exchanges. The dialyzed cell-free reaction product was loaded on an SEC (size-exclusion chromatography) column packed with Sepharose 6 FastFlow resin (GE Healthcare). The running buffer was the dialysis buffer with 5 mM DTT. Fraction were collected every 0.05 column volumes. The SEC fractions 9-11 were pooled and oxidized by the addition of 10 mM $H_2O_2$ or 10 mM diamide. The oxidized particles were then assessed using sucrose gradient centrifugation to indicate proper assembly. The protein concentrations of eluate fractions were determined based on radioactivity.

The production of the GLuc protein with an alkyne moiety was derived from the protocol described by Welsh et al, 2009, BBRC 389(4):563-8. Briefly, multiple 0.5 ml batch reactions were incubated at 30 C for 10 h in six-well polystyrene tissue-culture plates (Falcon Cat. No. 353046). Total and soluble protein concentrations were measured by liquid scintillation counting of L-[U-$^{14}$C]-leucine labeled proteins as described. Reactions were pooled and dialyzed against 100 volumes of Strep Load Buffer (SLB: 150 mM NaCl, 100 mM Tris-HCl, 1 mM EDTA, pH 8) for 12 h before loading onto a 1 ml Strep-Tactin Sepharose (IBA Gmbh, Gottingen, Germany) column which was equilibrated with 10 ml of SLB. Columns were washed three times with 1 ml SLB and eluted with 2.5 ml of Strep Elution Buffer (SEB: 150 mM NaCl, 100 mM Tris-HCl, 1 mM EDTA, 2.5 mM desthiobiotin, pH 8). The last 2 ml of the elution contained purified protein and was dialyzed against 2 L of 10 mM potassium phosphate buffer & 0.01% Tween 20, pH 8 for 12 h with three buffer exchanges, the last one containing 20% sucrose. Purified proteins were stored at −80° C. Purified protein samples were analyzed for purity by SDS-PAGE.

The synthesis of IM9-scFv with an alkyne moiety was derived from the protocol described by Patel et al. Briefly, multiple 0.5 ml batch reactions were incubated at 30 C for 10 h in the dark in six-well polystyrene tissue-culture plates (Falcon Cat. No. 353046). Total and soluble protein concentrations were measured by liquid scintillation counting of L-[U-$^{14}$C]-leucine labeled proteins as described. Reactions were pooled and dialyzed against 100 volumes of Strep Load Buffer (SLB: 150 mM NaCl, 100 mM Tris-HCl, 1 mM EDTA, pH 8) for 12 h before loading onto a 1 ml Strep-Tactin Sepharose (IBA Gmbh, Gottingen, Germany) column which was equilibrated with 10 ml of SLB. Columns were washed three times with 5 ml SLB and eluted with 2.5 ml of Strep Elution Buffer (SEB: 150 mM NaCl, 100 mM Tris-HCl, 1 mM EDTA, 2.5 mM desthiobiotin, pH 8). The last 2 ml of the elution contained purified protein and was dialyzed against 2 L of 10 mM potassium phosphate buffer, pH 8 for 12 h with three buffer exchanges, the last one containing 20% sucrose. Purified proteins were stored at −80° C. Purified protein samples were analyzed for purity by SDS-PAGE.

Azide-Alkyne conjugation and purification. The [3+2] cycloaddition click reactions were conducted in 1.5 mL microcentrifuge tubes in an anaerobic glovebox (Coy Laboratories, Grass Lake, Mich.) to preserve the reduced state of the tetrakis(acetonitrile)copper(I)hexafluorophosphate catalyst ([(CH$_3$CN)$_4$Cu]PF$_6$ or simply Cu (I) catalyst) (Sigma Aldrich, St. Louis, Mo.). Cu (I) catalyst was added to reactions at 2 mM in addition to 0.5 mM of the enhancer ligand, tris(triazolylmethyl)amine (TTMA), to improve the rate of the click reactions. HBc VLPs, IM9-scFv, and Gaussia Luciferase were mixed with the Cu (I) catalyst and TTMA enhancer with 0.01% Tween 20. Before addition of the Cu (I) catalyst, click reaction components were deoxygenated in microcentrifuge tubes for 1 h in the anaerobic glovebox. The click reactions for attaching functional molecules to HBc VLPs were conducted overnight. Samples from click reaction products were analyzed using SDS-PAGE and autoradiography. The nanoparticles were loaded on an SEC column packed with Sepharose 6 FastFlow resin (GE Healthcare). The running buffer was PBS with 0.01% Tween 20. Fraction were collected every 0.05 column volumes. The SEC fractions 9-15 were pooled and collected and stored in 4° C.

Cell Lines. A20, a BALB/c B cell lymphoma line, was obtained from ATCC (Manassas, Va.). Cells were cultured in medium which consisted of RPMI 1640 (Invitrogen) containing 2 mM glutamine, 100 units/ml penicillin-streptomycin, 10% FBS, and 50 µM 2-mercaptoethanol (Sigma-Aldrich). The A20 cell line expressing an anti-38C13 idiotype surface IgM (S1C5) was created by stable transfection with the expression vector described above using the Cell Line Nucleofector Kit V and a Nucleofector II electroporator (AMAXA Biosystems, Cologne, Germany). The transfected cells were cultured in the same media as the parental cell line with the addition of 800 µg/mL of Geneticin (Invitrogen). Cells were grown in suspension culture at 37° C. in in 5% $CO_2$. Cells density was determined by hemocytometry.

Cell enumeration method. B cell lymphoma cells were grown in culture medium to a high density. $5 \times 10^5$ A20 cells were spun down and resuspended in 100 µL RPMI 1640 media with 2 mM glutamine, 10% FBS, and 0.01% Pluronic F-68 (Sigma Aldrich). A known number of A20+S1C5 cells were added to the mixture.

For method 1, 10 µL of the collected nanoparticle mixture was added to the cell mixture and was allowed to incubate at 4° C. for 1 hour. The cell nanoparticle mixture was added to a 96-well MultiScreen HTS BV Filter Plate (Millipore MSBVS1210). The mixture was pulled down using the MultiScreen Vacuum Manifold (Millipore MAVM0960R). Immobilized cells were rinsed with culture medium. The medium was removed by the vacuum manifold. Prior to imaging, 20 uL of culture medium was added to wet the cells. 1 µL of 0.5 µg/µL coelentrazine (Nanolight, Pinetop, Ariz.) in propylene glycol was then added and pictures were taken after 30 secs.

For method 2, the cells mixture was pulled down with the vacuum manifold. 10 µL of the nanoparticle mixture was added to the immobilized cells and was allowed to incubate for 1 minute. Excess nanoparticles were rinsed away as described above. Photos were captured using a Nikon D90 using a 35 mm Nikkor lens with a Macro Extension Tube Ring (Fotodiox). Long exposures were performed with a Nikon 25395MC-DC2 Remote Release Cord.

Results and Discussions

The nanoparticle technology of the invention has both selective and specific interactions with specific cells, while generating enough light to be detected by a CCD camera. To demonstrate this enumeration method, we used a model B-cell system with A20 cells presenting the anti-38C13 idiotype (S1C5), known hereafter as marked cells and A20 cells known hereafter as unmarked cells. The marked cells specifically interact with the 38C13 scFv. Luminescent nanoparticles with specificity to these marked cells were prepared by using both single step conjugation and step two conjugation of the 38c13 IM9-scFv and the Gaussia luciferase to the HBc protein using click chemistry.

Figure 1:
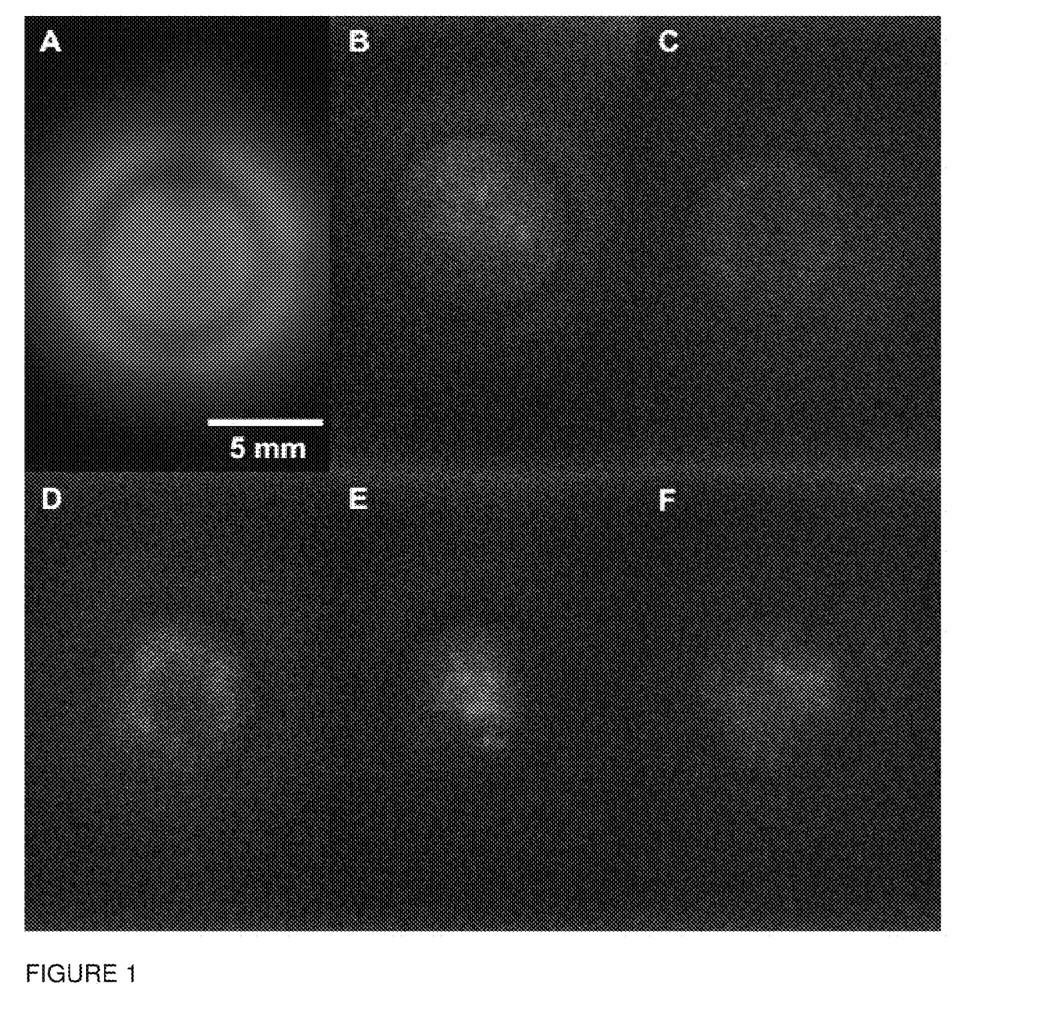
FIG. 1. CCD images of filter plate assay using method 1 as described in the Materials and Methods. All experiments included $5 \times 10^5$ A20 cells. Images were captured with a 120 sec exposure. A) A20 cells with no rinses. B) A20 cells with 1 rinse. C) A20 cells with 3 rinses. D) A20 cells and 400 S1C5 cells after 3 rinses. E) A20 cells and 200 S1C5 cells after 3 rinses. F) A20 cells and 100 S1C5 cells after 3 rinses.

Purified nanoparticles were added to a mixture of unmarked A20 cells in culture medium containing 10% FBS and 0.01% Pluronic F68. When the coelentrazine was added to the mixtures, light was generated suggesting that the nanoparticles have luciferase activity. To reduce non-specific binding, the cells were washed with culture medium containing 10% FBS and 0.01% F68. As additional washes were performed the background light generated by nonspecifically bound luciferase diminishes. (FIG. 1*a-c*)

When a known number of marked cells were added to the mixture which included the nanoparticles, a noticeable increase in overall light intensity compared to the no marked cell control can be noticed. The increase in light is correlated with the number of added cells. However, it was also noticed that the spots of light were inconsistently sized. Light coming from a single cell should be the size of a pixel. However, these spots are indicative of spots several microns wide, reflective of cell aggregation. The frequency of these clumps decrease as fewer cells were added. (FIG. 1*d-f*) This indicates that the nanoparticles simultaneously attach to two marked cells as crosslinkers to flocculate the marked cells. This feature may be used to enrich, collect, and isolate rare cells.

In addition, the same approach can be used to enumerate and/or collect cells with characterized by a unique combination of markers. For example, to isolate rare stem cells characterized by the presence of marker A and the absence of marker B, cells would first be isolated using nanoparticles presenting an antibody fragment that binds to marker A. Cells with marker A would be flocculated, and this group would contain some cells that also present marker B as well as the desired cells that do not. These cells would be resuspended by adding a specific protease that releases the antibody fragment from the nanoparticles thereby releasing the aggregated cells from each other. Next a second nanoparticle with a surface antibody fragment binding to marker B would be used to flocculate the cells with marker B so that only the desired cells will then remain in suspension. These can then be enumerated and collected by standard techniques.

Figure 2:
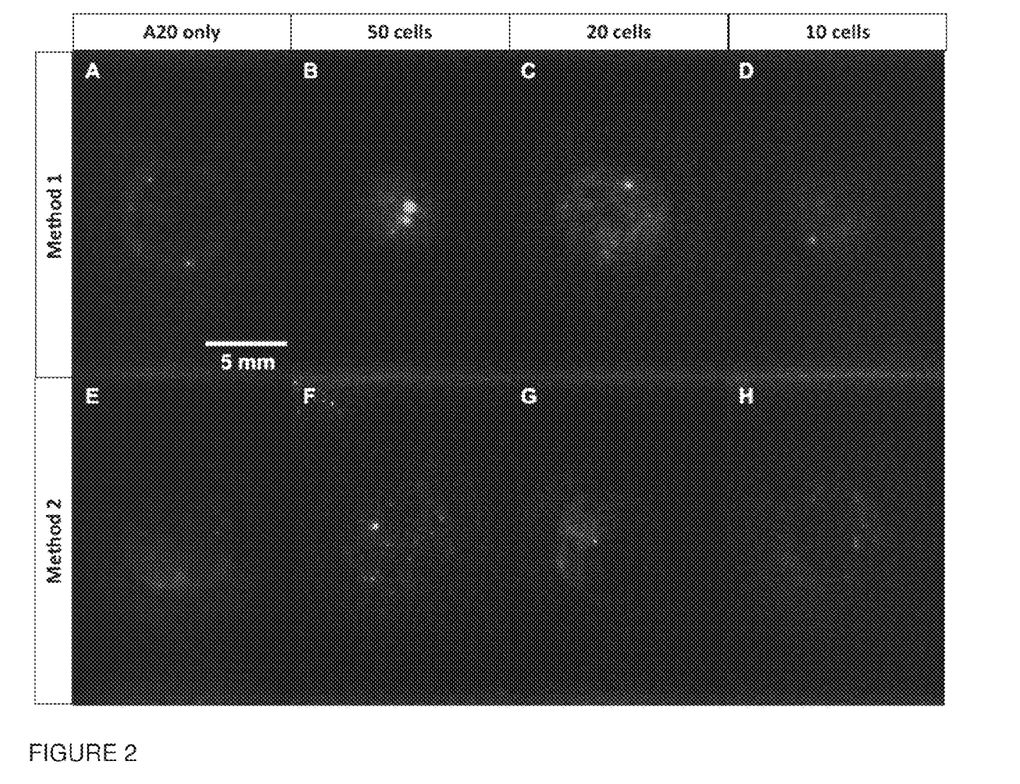
FIG. 2. CCD images of filter plate assay comparing method 1 and method 2 as described in the Materials and Methods. All experiments included $5 \times 10^5$ A20 cells and 4 rinses. All images were captured with a 600 sec exposure. A-D) Method 1 with A20 cells only, 50 S1C5 cells, 20 S1C5 cells, and 10 S1C5 cells respectively. E-H) Method 2 with A20 cells only, 50 S1C5 cells, 20 S1C5 cells, and 10 S1C5 cells respectively.

For enumeration, it can be more straightforward to count individual spots rather than total light intensity. Rather than add the nanoparticles to mixture, the nanoparticle mixture was added after the cells were immobilized on the filter plate. This prevents cell aggregation and larger spots of light. The delayed addition of nanoparticles, allowed resolution of fine spots of light, where the total light intensity is correlated with the number of added marked cells. (FIG. 2)

What is claimed is:

1. A method of detecting a rare circulating cell in a blood sample, present at a concentration of less than 1 in $10^5$ in the population, the method comprising:
   contacting the sample with an effective amount of a labeling nanoparticle, wherein the labeling nanoparticle comprises a virus-like particle (VLP) directly conjugated by covalent bonds to (i) a plurality of light emitting moieties; and (ii) a plurality of specific binding moieties that selectively bind to the circulating cell;
   washing the sample free of unbound labeling nanoparticle wherein the sample is immobilized on a membrane prior to contacting the labeling nanoparticle or following contacting with the labeling nanoparticle;
   contacting the washed sample with a substrate for the light emitting moiety; and
   quantitating the emission of light, wherein the presence of light is indicative of the presence of the circulating cell, wherein the method is performed in the absence of affinity based enrichment of cells.

2. The method of claim 1, wherein the VLP is comprised of Hepatitis B virus core protein.

3. The method of claim 1, wherein the covalent binding is through unnatural amino acids present on the VLP and moieties.

4. The method of claim 1, wherein the light emitting moieties are luciferase proteins.

5. The method of claim 4, wherein from 5 to 60 luciferase proteins are conjugated to the nanoparticle.

6. The method of claim 1, wherein the specific binding moieties are antibodies or a fragment thereof.

7. The method of claim 6, wherein from 1 to 50 antibody proteins are conjugated to the nanoparticle.

8. The method of claim 1 wherein the circulating cell is a circulating tumor cell.

9. The method of claim 1 wherein the circulating cells are present at a concentration of less than 1 in $10^5$ cells in the sample.

10. The method of claim 1, wherein the blood sample is a sample from an individual suspected of having residual cancer.

* * * * *